(12) United States Patent
Rogers et al.

(10) Patent No.: US 8,182,158 B2
(45) Date of Patent: May 22, 2012

(54) FIXTURE FOR SHAPE-SENSING OPTICAL FIBER IN A KINEMATIC CHAIN

(75) Inventors: Theodore W. Rogers, Alameda, CA (US); Giuseppe Prisco, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 12/878,162

(22) Filed: Sep. 9, 2010

(65) Prior Publication Data

US 2011/0044578 A1 Feb. 24, 2011

Related U.S. Application Data

(63) Continuation of application No. 12/164,297, filed on Jun. 30, 2008, now Pat. No. 7,815,376.

(51) Int. Cl.
*G02B 6/38* (2006.01)
(52) U.S. Cl. ............................................. 385/66; 606/2
(58) Field of Classification Search ............ 385/12, 385/66; 606/2, 4, 138
See application file for complete search history.

(56) References Cited

U.S. PATENT DOCUMENTS

| | | | |
|---|---|---|---|
| 4,806,012 A | 2/1989 | Meltz et al. | |
| 5,321,257 A | 6/1994 | Danisch | |
| 5,370,675 A | 12/1994 | Edwards et al. | |
| 5,607,435 A | 3/1997 | Sachdeva et al. | |
| 5,633,748 A | 5/1997 | Perez et al. | |
| 5,789,890 A | 8/1998 | Genov et al. | |
| 5,846,247 A | 12/1998 | Unsworth et al. | |
| 5,873,865 A | 2/1999 | Horzewski et al. | |
| 5,876,373 A | 3/1999 | Giba et al. | |
| 5,885,258 A | 3/1999 | Sachdeva et al. | |
| 5,915,056 A * | 6/1999 | Bradley et al. | 385/76 |
| 5,935,119 A | 8/1999 | Guy et al. | |
| 5,946,436 A | 8/1999 | Takashi | |
| 5,993,447 A | 11/1999 | Blewett et al. | |
| 5,995,875 A | 11/1999 | Blewett et al. | |
| 6,004,639 A | 12/1999 | Quigley et al. | |
| 6,047,094 A | 4/2000 | Kalamkarov et al. | |
| 6,056,743 A | 5/2000 | Ellis et al. | |
| RE36,833 E | 8/2000 | Moore et al. | |

(Continued)

FOREIGN PATENT DOCUMENTS

EP 1113299 A2 * 7/2001

(Continued)

OTHER PUBLICATIONS

Vertut, Jean and Philippe Coiffet, *Teleoperation and Robotics: Evolution and Development*, English translation Prentice-Hall, Inc., Inglewood Cliffs, NJ, USA, 1986, 332 pages.

*Primary Examiner* — Charlie Peng
*Assistant Examiner* — Peter Radkowski

(57) ABSTRACT

Localized strain is effectively eliminated in a shape sensing optical fiber where the fiber exits a link in a kinematic chain. In one aspect, the fiber is positioned in a channel within a fiber fixture portion of the link, and a surface of a lip of the channel is curved. The curved surface of the lip begins tangent to a wall of the channel and has a maximum radius of curvature that is less than the minimum bend radius that the fiber will experience during shape sensing. In another aspect, the fiber is positioned within a shape memory alloy tube that extends from the link.

19 Claims, 5 Drawing Sheets

U.S. PATENT DOCUMENTS

| | | | |
|---|---|---|---|
| 6,102,932 A | 8/2000 | Kurz | |
| 6,106,521 A | 8/2000 | Blewett et al. | |
| 6,127,672 A | 10/2000 | Danisch | |
| 6,215,943 B1 | 4/2001 | Crotts et al. | |
| 6,256,090 B1 | 7/2001 | Chen et al. | |
| 6,278,811 B1 | 8/2001 | Hay et al. | |
| 6,296,622 B1 | 10/2001 | Kurz et al. | |
| 6,319,267 B1 | 11/2001 | Kurz | |
| 6,396,572 B1 | 5/2002 | Chang et al. | |
| 6,443,944 B1 * | 9/2002 | Doshi et al. | 606/1 |
| 6,470,205 B2 | 10/2002 | Bosselmann et al. | |
| 6,471,710 B1 | 10/2002 | Bucholtz | |
| 6,491,689 B1 | 12/2002 | Ellis et al. | |
| 6,586,722 B1 | 7/2003 | Kenny et al. | |
| 6,612,992 B1 | 9/2003 | Hossack et al. | |
| 6,652,491 B1 * | 11/2003 | Walker et al. | 604/164.01 |
| 6,706,348 B2 | 3/2004 | Quigley et al. | |
| 6,728,431 B2 | 4/2004 | Ames et al. | |
| 6,854,327 B2 | 2/2005 | Rambow et al. | |
| 6,858,005 B2 | 2/2005 | Ohline et al. | |
| 6,872,433 B2 | 3/2005 | Seward et al. | |
| 6,946,645 B2 | 9/2005 | Tarvin et al. | |
| 6,987,897 B2 | 1/2006 | Elster et al. | |
| 7,194,296 B2 | 3/2007 | Frantz et al. | |
| 7,277,162 B2 | 10/2007 | Williams | |
| 7,338,434 B1 * | 3/2008 | Haarstad et al. | 600/37 |
| 7,338,505 B2 | 3/2008 | Belson | |
| 7,379,632 B1 | 5/2008 | Twerdochlib | |
| 2001/0021843 A1 * | 9/2001 | Bosselmann et al. | 606/2 |
| 2002/0016598 A1 | 2/2002 | Kurz | |
| 2002/0054747 A1 * | 5/2002 | Foley | 385/134 |
| 2002/0120260 A1 | 8/2002 | Morris et al. | |
| 2002/0120261 A1 | 8/2002 | Morris et al. | |
| 2002/0142119 A1 | 10/2002 | Seward et al. | |
| 2002/0173817 A1 | 11/2002 | Kletschka et al. | |
| 2002/0188285 A1 | 12/2002 | Brown | |
| 2003/0045778 A1 | 3/2003 | Ohline et al. | |
| 2003/0060782 A1 | 3/2003 | Bose et al. | |
| 2003/0072515 A1 | 4/2003 | Ames et al. | |
| 2004/0012363 A1 | 1/2004 | Simondet | |
| 2004/0054322 A1 * | 3/2004 | Vargas | 604/95.04 |
| 2004/0096614 A1 | 5/2004 | Quigley et al. | |
| 2004/0165810 A1 | 8/2004 | Fujita | |
| 2005/0154261 A1 | 7/2005 | Ohline et al. | |
| 2005/0154379 A1 * | 7/2005 | McGowan et al. | 606/4 |
| 2006/0045408 A1 | 3/2006 | Jones et al. | |
| 2007/0123913 A1 * | 5/2007 | Beulke et al. | 606/138 |
| 2007/0151391 A1 | 7/2007 | Larkin et al. | |
| 2007/0156019 A1 | 7/2007 | Larkin et al. | |
| 2007/0177008 A1 | 8/2007 | Bayer et al. | |
| 2008/0154288 A1 | 6/2008 | Belson | |
| 2008/0214999 A1 | 9/2008 | Kletschka et al. | |
| 2008/0216826 A1 | 9/2008 | Boyden et al. | |
| 2008/0216840 A1 | 9/2008 | Boyden et al. | |
| 2008/0218770 A1 | 9/2008 | Moll et al. | |
| 2008/0285909 A1 | 11/2008 | Younge et al. | |
| 2009/0022450 A1 * | 1/2009 | Song et al. | 385/12 |

FOREIGN PATENT DOCUMENTS

| | | | | |
|---|---|---|---|---|
| JP | 59121305 A | * | 7/1984 | |
| JP | 60184975 A | * | 9/1985 | |
| JP | 06339787 A | * | 12/1994 | |
| JP | 08308934 A | * | 11/1996 | |
| JP | 11048171 A | * | 2/1999 | |
| JP | 2001155268 A | * | 6/2001 | |
| JP | 2007154997 A | * | 6/2007 | |
| WO | WO 9104433 A | * | 4/1991 | |

* cited by examiner

FIXTURE FOR SHAPE-SENSING OPTICAL FIBER IN A KINEMATIC CHAIN

This application is a continuation of U.S. patent application Ser. No. 12/164,297 (filed Jun. 30, 2008; now U.S. Pat. No. 7,815,376), which is incorporated by reference herein its entirety.

BACKGROUND

1. Field of Invention

The invention relates to fiber optic sensors, and more particularly to fiber optic sensors for detecting the fiber's position and orientation, and still more particularly to fixtures used to constrain a fiber optic sensor with reference to a link in a kinematic chain.

2. Art.

In shape sensing systems that use interferometric techniques to interrogate an optical glass fiber with refractive index change (Bragg) gratings, the physical resources of the interrogating hardware limit the number of data points that can be used to describe the fiber's shape at any particular time. Specifically, the product of the capacity of the interrogator's electronic data processor and the interrogating laser's frequency sweep range is approximately proportional to the product of the length of the fiber being sensed and the peak strain that occurs within the sensed length. Bending is typically the primary source of strain in an optical fiber used as a shape sensor. The peak strain effectively occurs at the point of minimum bend radius in the sensed portion of the fiber.

In order to use a fiber optic shape sensor in a kinematic chain, such as a robot manipulator arm, it is often useful to constrain one or more portions of the sensed length in known positions and/or orientations relative to the individual links in the chain. Known ways of holding an optical fiber in place include the use of collets and various other mechanical clamping mechanisms, as well as gluing, etc. When applied to a moveable joint, however, many of these methods of holding a fiber result in a point load being applied to a location along the fiber, which results in exceedingly large peak strains at that location. What is required is a way to effectively eliminate these large peak strains.

SUMMARY

In a kinematic chain that includes a first link, a second link, and a joint that couples the first and second links, an optical fiber extends between the first and second links across the joint. The optical fiber is configured with fiber Bragg gratings for shape sensing.

In one aspect, the fiber bends as the joint moves, and therefore a minimum bend radius for the fiber is defined when the joint reaches a limit in its range of motion. A fixture is associated with the first link and constrains the fiber with reference to the first link. The fiber is positioned within a channel in the fixture, and a length of fiber Bragg gratings in the fiber is positioned adjacent a lip of the channel. A surface of the lip is curved in one or more of the planes in which the fiber may bend due to the joint's movement. The curved surface begins tangent to a wall of the channel, and the maximum radius of curvature of the curved surface that may contact the fiber is less than the minimum bend radius of the fiber that has been defined by the joint's range of motion. The curved surface of the lip effectively eliminates the localized strain in the shape sensing optical fiber where the fiber exits the link in the kinematic chain.

In another aspect, the shape-sensing optical fiber is positioned within a shape memory alloy tube that extends between the first and second links in the kinematic chain. The optical fiber is positioned such that the length of fiber Bragg gratings in the fiber is adjacent the location where the shape memory alloy tube extends from the first link.

DETAILED DESCRIPTION

This description and the accompanying drawings that illustrate aspects, implementions, and embodiments of the present invention should not be taken as limiting—the claims define the protected invention. Various mechanical, compositional, structural, electrical, and operational changes may be made without departing from the spirit and scope of this description and the claims. In some instances, well-known circuits, structures, and techniques have not been shown or described in detail in order not to obscure the invention. Like numbers in two or more figures represent the same or similar elements.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes includes various special device positions and orientations.

In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. All examples and illustrative references are non-limiting and should not be used to limit the claims to specific implementations and embodiments described herein and their equivalents.

Figure 1:
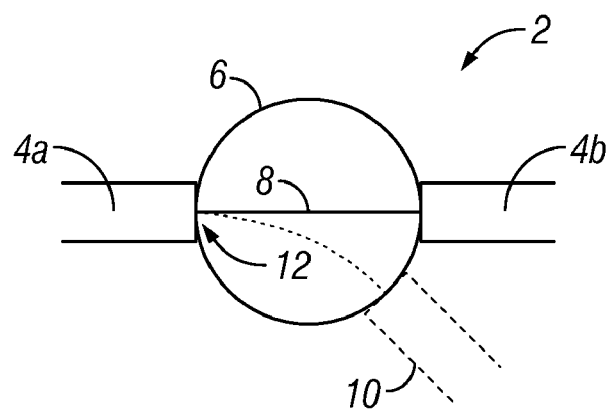
FIG. 1 is a diagrammatic view of a portion of a kinematic chain.

FIG. 1 is a diagrammatic view of a portion of an illustrative kinematic chain 2. Two links 4a, 4b are coupled by a revolute joint 6. For illustrative purposes only, joint 6 is a single degree-of-freedom (DOF) joint. The joint may, however, have two or more DOFs. In addition, the joint may be a "flexible" component—a continuously bending structure or a "snake-like" mechanism that includes one or more additional small links that function as "vertebrae" as the mechanism bends. It should be understood that such "flexible" components may be considered and modeled as a single joint.

A shape sensing optical glass fiber 8 extends between the links 4a, 4b through joint 6. As shown in detail below, optical fiber 8 extends through a channel that opens out of link 4a. The fiber may exit the link essentially on the link's centerline, or the fiber may be offset from the link's centerline. For clarity, most of this description refers to a fiber that exits at the link's centerline, but it should be understood that the description refers to a fixture that aligns the fiber in various ways with a link (e.g., through the link on or off centerline, at the link's outer perimeter, beside the link, and the like). FIGS. 7A-7D below illustrate fiber/link alignment aspects in more detail.

Shape sensing optical glass fiber 8 is configured with closely spaced refractive index change (Bragg) gratings that allow strain to be sensed at multiple locations along the fiber using known methods. In one instance the fiber is a three-core fiber with each core configured with substantially parallel Bragg gratings approximately 22 mm long and spaced apart by less than ¼ mm. In one instance, approximately 60 longitudinally adjacent Bragg gratings are formed for every 20 mm length of a core/fiber. Accordingly, the resolution of the sensed strain at various fiber locations along the fiber's longitudinal (proximal to distal end) axis is on the order of microns, which allows for accurate shape sensing. This optical fiber description applies to all optical fibers referred to herein.

If optical fiber 8 is fixed with reference to the links 4a, 4b, then the length of fiber 8 between the links 4a, 4b is constant as the joint rotates (if the fiber is unconstrained within the joint, the fiber may bow or loop in various ways during the joint rotation). If optical fiber 8 translates with reference to either or both links 4a, 4b, then the length of fiber 8 between the links 4a, 4b may vary (if the fiber is unconstrained within the joint, the fiber's stiffness may cause it to slide within one or both links when the joint bends). Optical fiber 8 may be fixed in orientation with reference to the links 4a, 4b. Alternately, the fiber may roll. Using known shape sensing technology, which may be combined with known inverse kinematic calculations by an electronic data processing system, the position and orientation of link 4b may be determined with reference to link 4a.

As the joint rotates, as illustrated by alternate position 10 shown in FIG. 1, link 4b changes in orientation with reference to link 4a by an angle θ. Accordingly, optical fiber 8 bends, and the fiber bend is expressed in terms of the fiber's bend radius. The bend radius may vary considerably over the length of the bend in order to fit the mechanics of a particular joint or set of joints. At one or more fiber locations between the links, a minimum fiber bend radius occurs at each joint angle θ.

Figure 2A:
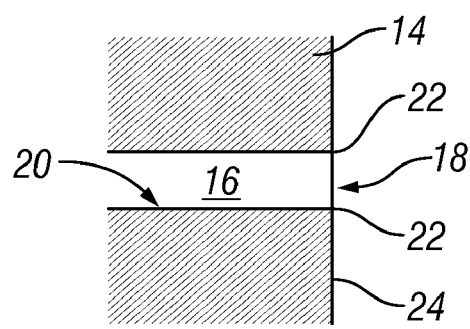
FIG. 2A is a diagrammatic cross-sectional view of a fixture portion of a link in a kinematic chain.
Figure 2B:
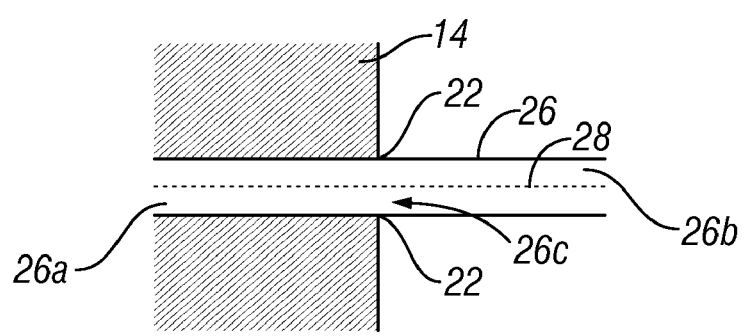
FIG. 2B is a diagrammatic cross-sectional view of a shape-sensing optical fiber mounted in a fixture portion of a link in a kinematic chain.
Figure 2C:
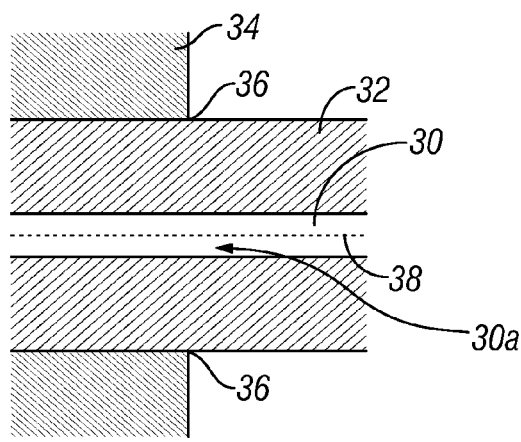
FIG. 2C is a diagrammatic cross-sectional view of another assembly for a shape-sensing optical fiber mounted in a fixture portion of a link in a kinematic chain.

It has been discovered that for known ways of combining a link and an optical fiber, that as the joint moves and the fiber bends, a peak strain occurs in the fiber at a location 12 where the fiber exits the link. This peak strain saturates the strain interrogation equipment, a condition which causes a loss in the shape sensor's accuracy and update speed. For purposes of this disclosure, this situation may be termed a localized strain saturation problem. FIGS. 2A-2C illustrate this situation in more detail.

FIG. 2A is a diagrammatic cross-sectional view of fixture portion 14 of a link in a kinematic chain. Fixture portion 14 supports a shape sensing optical fiber as the fiber exits the link into a joint region of the kinematic chain. A channel 16 is defined in the fixture portion, and the channel opens to the joint region at an opening 18. The channel 16 has a channel wall 20. A lip 22 exists between the channel wall 20 and the end 24 of fixture portion 14. For example, fixture portion 14 is illustrative of a Newport Corporation Delrin-jawed fiber chuck (part no. FPH-DJ).

FIG. 2B is a diagrammatic cross-sectional view of a shape-sensing optical fiber 26 mounted in fixture portion 14. Optical fiber 26 extends through channel 16 and exits fixture portion 14 via opening 18. A first portion 26a of the optical fiber is positioned within fixture portion 14 of a link in the kinematic chain. A second portion 26b of the optical fiber extends beyond the link in the kinematic chain and is illustrative of the portion of a shape-sensing optical fiber that extends into or through a joint in the kinematic chain. Both portions 26a and 26b are in the portion of the optical fiber that is being interrogated for strain information in a shape-sensing system. As portion 26b bends as the joint rotates, the optical fiber 26 experiences a peak strain at a location 26c, adjacent lip 22. The dotted line 28 represents the fiber Bragg gratings (FBG's) in the fiber's cores that are interrogated for strain measurement. Accordingly, a length of interrogated FBG's that experience the peak strain is adjacent lip 22. The term fiber Bragg grating should be broadly construed to include the many variations of such refractive index change gratings.

FIG. 2C is an illustrative diagrammatic cross-sectional view of another mounting assembly for a shape-sensing optical fiber. As shown in FIG. 2C, shape-sensing optical fiber 30 is surrounded by Teflon® FEP tube 32. In one implementation, tube 32 has an approximately 0.4 mm inner diameter and 1.5 mm outer diameter. Tube 32 is then mounted in fixture portion 34 in a manner similar to the way fiber 26 is mounted in fixture portion 14, as shown in FIG. 2B. Since Teflon® FEP is a relatively soft material, it was thought that the Teflon® FEP tube 32 would cushion optical fiber 30 against lip 36 as the fiber and tube were bent during joint movement. It was discovered, however, that as the bend radius of the tube and fiber decreases, the reactive force from lip 34 is transmitted through the Teflon® FEP tube 32 to the fiber 30, which again causes a localized peak strain in fiber 30 in the length of FBG's 38 in the vicinity of region 30*a*, which is roughly adjacent to lip 36. Once again, the localized strain saturation problem occurs.

The inventors have discovered how to effectively eliminate the region of peak strain in the length of shape sensing FGB's adjacent the channel lip where the optical fiber exits the fixture for all fiber bend radii down to the minimum allowed by the material constraints of the fiber.

Figure 3A:
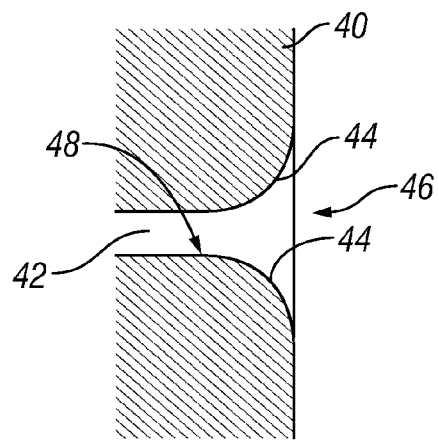
FIG. 3A is a cross-sectional diagrammatic view of another optical fiber fixture portion of a link in a kinematic chain.

FIG. 3A is a cross-sectional diagrammatic view of an optical fiber fixture portion 40 in accordance with an aspect of the invention. Fixture portion may be at the end of a link in a kinematic chain. One non-limiting example of such a kinematic chain is a telerobotically controlled minimally invasive surgical instrument, such as those used in the da Vinci® Surgical System manufactured by Intuitive Surgical, Inc. of Sunnyvale, Calif. Fixture portion 40 may be integral with the material used to form the link, or it may be one or more separate devices that are coupled to the link. Non-limiting examples of such devices are various collets, chucks, and split clamp mechanisms that may be used to hold or constrain an optical fiber. Aspects of the invention as described herein apply to any and all such ways to hold/constrain an optical fiber.

As shown in FIG. 3A, a channel 42 is defined in fixture portion 40. In contrast to FIGS. 2A-2C, the lip 44 at the opening 46 where the optical fiber exits the fixture portion is curved. There are several characteristics to the curve of lip 44. First, the curve begins substantially tangent to channel wall 48 (small fabrication anomalies typically prevent making a geometrically perfect tangential transition, but known fabrication methods, e.g. electrical discharge machining with a shaped electrode, allow such a transition to be substantially and effectively achieved). Second, the maximum radius of curvature for lip 44 is less than the minimum bend radius that the shape-sensing optical fiber will experience—the bend that the fiber experiences as the joint moves to its maximum allowable angle $\theta_{MAX}$—so that the fiber remains tangent to the curve of the lip as the fiber bends through its full range of motion. This maximum radius of curvature limitation for the lip applies everywhere on the curved lip surface that substantially intersects a bending plane of the fiber (again, known fabrication methods can be used to effectively create the curved surface, despite small fabrication anomalies that may occur). Further, the radius of curvature of the lip surface need not be constant. And, in addition, the lip's radius of curvature should not be so small as to effectively create an abrupt edge, which causes localized strain in the fiber as discussed above. As a guide for fabrication, a minimum radius of curvature for lip 44 may be considered to be approximately ¼ to ½ the fiber's minimum bend radius at the joint's $\theta_{MAX}$, although a smaller bend radius is likely acceptable in many applications.

It should be understood that many types of joints exist, and that the minimum bend radius referred to herein is the minimum bend radius of the portion of the fiber in free space immediately adjacent the link from which the fiber extends. In a "snake-like" joint referred to above, for example, the minimum bend radius of the fiber that is used to determine the radius of curvature for the curved surface of the lip would be in the portion of fiber that extends between the link and the first "vertebra" link in the joint.

For single-DOF joint implementations, the curve of the lip need only be coplanar with the plane in which the fiber bends. In other implementations, including single- and multi-DOF joints that allow three-dimensional (3D) position and orientation changes, such as for a multi-DOF ball and socket joint or for a shape sensing optical fiber that spans multiple single-DOF joints, the lip may be formed in three-dimensions in a "trumpet-like" shape. In some implementations, the 3D shape may be tailored to fit the range of motion of the joint in each direction which it is allowed to move, creating shapes that are ellipsoid or multiply fluted in cross-section to allow for the resulting fiber bend directions. Further, the channel may have various shapes, such as a cylinder that closely fits around the fiber (either (i) not permitting the fiber to slide, or (ii) permitting the fiber to slide only in a longitudinal direction with reference to the link and to roll or twist within the channel) or a slit (e.g., effectively the width of the fiber's outer diameter) that permits the fiber to move within the plane of the slit. Various low friction materials and coatings (e.g., Teflon® FEP tube, Teflon® coating) may be used to facilitate fiber sliding within the channel.

Figure 3B:
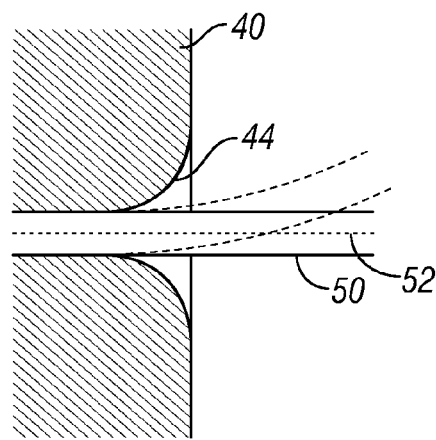
FIG. 3B is a cross-sectional diagrammatic view of a shape-sensing optical fiber mounted in a fixture portion of a link in a kinematic chain.

FIG. 3B is a cross-sectional diagrammatic view of an illustrative implementation of a shape sensing optical fiber 50 mounted in fixture portion 40 in accordance with aspects of the invention. As shown in FIG. 3B, as fiber 50 bends (shown by the dashed lines) with joint rotation, the fiber remains essentially tangent to the curved lip 44 at the channel's opening (lip 44 is shown curved on both sides of the channel in anticipation of the fiber bending in both directions, but need be curved only in the direction the fiber will bend in a particular embodiment). The region of peak strain is effectively eliminated in the length of FBG's 52 that is in the vicinity of the curved lip. This length of FBG's is a portion of the FBG's that are interrogated for strain information used to determine fiber shape based on the associated joint movement.

Figure 4:
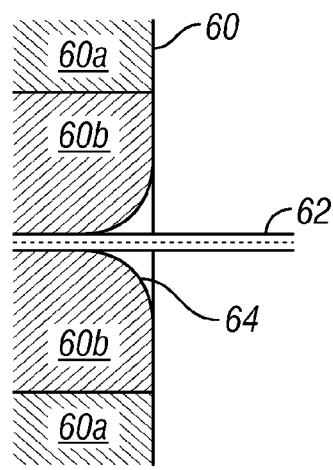
FIG. 4 is another cross-sectional diagrammatic view of a shape-sensing optical fiber mounted in a fixture portion of a link in a kinematic chain.

Although the implementation illustrated by FIG. 3B is effective, it may be difficult to create the long, small diameter due to, e.g., drill limitations. Accordingly, a similar fixture may be made as depicted in FIG. 4. FIG. 4 is another illustrative cross-sectional diagrammatic view of a portion of an optical fiber fixture 60 in accordance with an aspect of the invention. In the exemplary implementation shown in FIG. 4, the fixture portion includes two pieces. A relatively larger channel is created in a first piece 60*a*, and then a second piece 60*b* having a preformed, relatively smaller channel is inserted into the channel in piece 60*a*. An optical glass fiber 62 is positioned within the relatively smaller channel in second piece 60*b*. This aspect allows a larger channel to be formed in piece 60*a* using conventional methods (e.g., drilling), and then a tube having the required inner diameter for the fiber can be inserted as piece 60*b* into the channel in piece 60*a*. The curved lip 64 where the fiber channel leaves the fixture portion 60 and enters the joint region is formed in the second piece.

In an illustrative test assembly implementation (see e.g., FIG. 8), a first fixture piece 60*a* was formed using a fused deposition modeling (FDM) process, and a PEEK tube was used as the second fixture piece 60*b*. The inner diameter of the PEEK tube was approximately 0.016-inch, so that a shape sensing optical glass fiber could be held within the tube 60*b*. The curved, tangential lip 64 was formed using a radius cutting center drill having an approximately ¹⁄₆₄-inch tip diameter and an approximately ¹⁄₁₆-inch radius curved shoulder.

Figure 5:
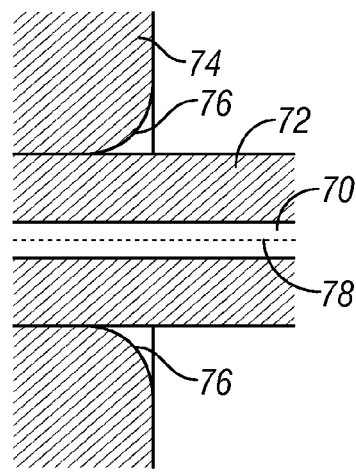
FIG. 5 is yet another cross-sectional diagrammatic view of a shape-sensing optical fiber mounted in a fixture portion of a link in a kinematic chain.

FIG. 5 is another cross-sectional diagrammatic view of a portion of a fixture for a shape sensing optical fiber. As shown in FIG. 5, a shape-sensing optical fiber 70 is positioned inside a flexible tube 70, and the combined fiber 70 and tube 72 is positioned in the portion of the fixture 74. Similar to the aspects shown and described above, the lip 76 of the channel in which the combined fiber and tube is positioned is curved. The curve of lip 76 is determined from the minimum bend radius of the fiber as described above, not from the minimum bend radius of the flexible tube 72. In one non-limiting, illustrative implementation the flexible tube 72 is a Teflon® FEP tube as described above. The use of a Teflon® FEP tube may be beneficial in certain implementations, such as those in which the fiber translates along a longitudinal axis of a link as a joint bends due to, e.g., a reaction to changes in length of the minimum energy fiber path in free space as the joint bends, or the fiber being offset from the link's centerline. Additional benefits of using a protective tube around the fiber include protection for soft coatings, such as acrylate, on the fiber.

Skilled artisans will understand that FIGS. 3A, 3B, 4, and 5 are illustrative of various ways of holding an optical fiber. Curved lip aspects of the invention may be applied to, e.g., various fiber collet and chuck mechanisms, split clamp mechanisms, grooves with the fiber positioned therein, etc. Skilled artisans will also understand that various aspects as shown and described herein may be combined. As a non-limiting example, a two-piece portion of the fixture assembly as illustrated by FIG. 4 may be used together with the combined flexible tube and fiber as illustrated by FIG. 5.

Figure 6:
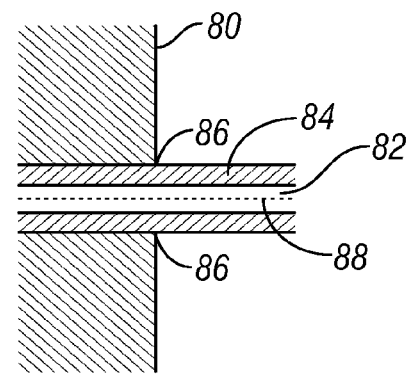
FIG. 6 is still another cross-sectional diagrammatic view of a shape-sensing optical fiber mounted in a fixture portion of a link in a kinematic chain.

FIG. 6 is another cross-sectional diagrammatic view of a portion of a fixture 80 for a shape sensing optical fiber. In accordance with another aspect of the invention, an FBG-configured shape-sensing optical fiber 82 is surrounded by a tube 84 of shape memory alloy/superelastic material, such as a Nickel/Titanium alloy. In this aspect of the invention, the lip 86 of the channel that opens into the joint region is not curved. Instead, as fiber 82 bends, tube 84 distributes the reactive forces from lip 86 along the fiber 82 sufficient to avoid producing a region of local strain in the length of FBG's 88 that is adjacent the lip. In one illustrative, non-limiting implementation, tube 84 is a Nitinol tube having a 0.016-inch inner diameter and a 0.026-inch outer diameter. This Nitinol tube allows for an effective minimum bend radius for the fiber in the range of 10-15 mm or less, which is on the order of half that which could be obtained with a non-superelastic material.

Figure 7A:
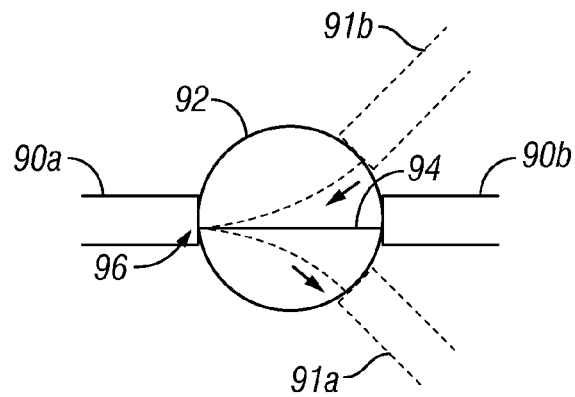
FIGS. 7A-7D are diagrammatic views that illustrate various ways that a fixture portion may be positioned with reference to a link.

FIGS. 7A-7D are diagrammatic views that illustrate various ways that the fixture portion may be positioned with reference to a link. FIG. 7A shows two links 90a, 90b coupled by a revolute joint 92. A shape sensing optical fiber 94 runs between links 90a and 90b, through the region of joint 92. As shown in FIG. 7A, the fixture portion 96 (as described above with reference to FIGS. 3A-6) that holds/constrains fiber 94 is offset from the centerlines of links 90a, 90b (for clarity, fixture portion 96 is indicated only for link 90a, but may also be used for link 90b if strain interrogation occurs beyond the location where fiber 94 enters link 90b). In some instances, optical fiber 94 may have to translate (slide) with reference to one or both links as joint 92 rotates. As a non-limiting example, if fiber 92 is fixed in position with reference to link 90a and allowed to translate with reference to link 90b, then fiber 92 may translate in the directions shown by the arrows as link 90b moves to alternate positions 91a and 91b because of the fiber's offset from the link centerlines. Consequently, the length of FBG's adjacent the lip of the channel also slides, but the curved lip effectively eliminates peak strain from occurring in the FBG's.

Figure 7B:
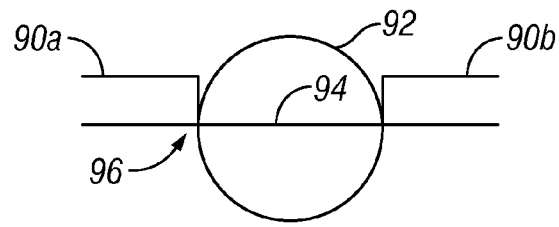

FIG. 7B illustrates that a fixture portion may be positioned so that the fiber is generally aligned with an outer perimeter of link 90a. As a non-limiting example, a groove may be made in an outer surface of the link, and the shape-sensing fiber may then be laid into the groove and affixed by, e.g., clamping, gluing, etc. As discussed with reference to FIG. 7A, the fiber may be allowed to translate with reference to either or both links 90a, 90b as the joint rotates.

Figure 7C:
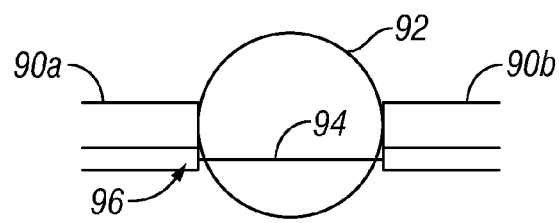

FIG. 7C illustrates that a fixture portion may be separate from link 90a and mechanically coupled in any of various conventional ways.

Figure 7D:
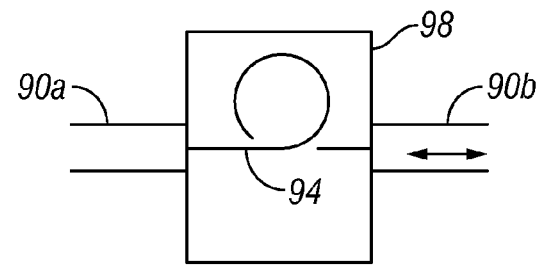

FIG. 7D illustrates that aspects of the invention are not confined to use with single-DOF revolute joints. As a non-limiting example, links 90a and 90b may be coupled by a prismatic joint 98, and shape-sensing optical fiber 94 is looped in the joint region to accommodate relative translation (i.e., surge) between links 90a and 90b, as indicated by the double-headed arrow. Various other loop shapes (e.g., omega-shaped) may be used.

Figure 8:
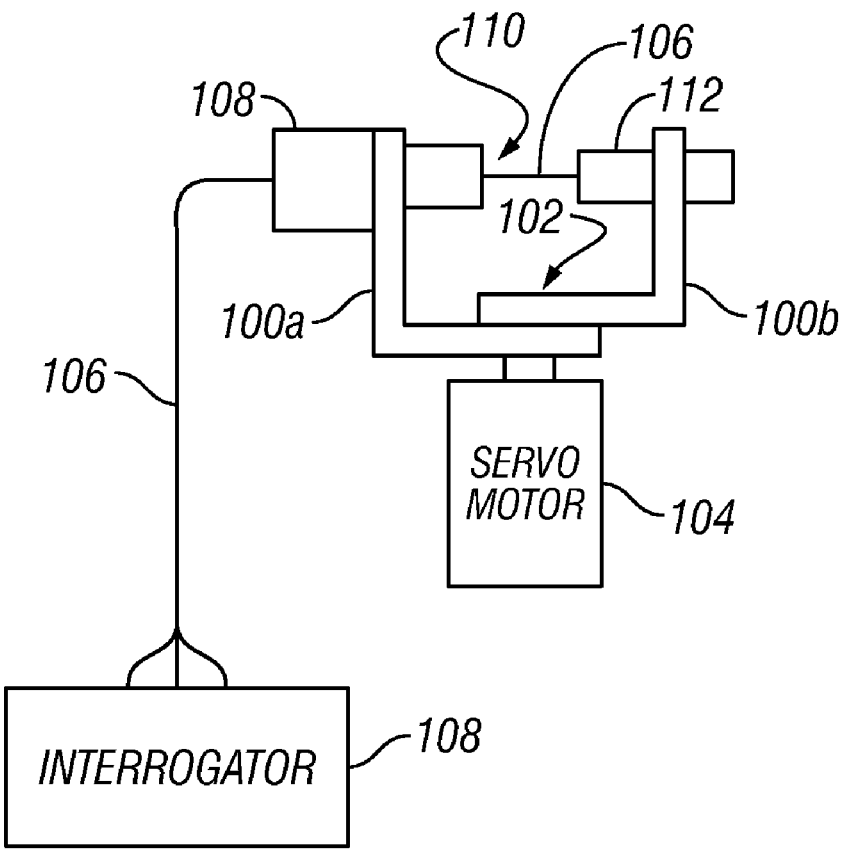
FIG. 8 is a diagrammatic front elevation view of a test apparatus.

FIG. 8 is a diagrammatic front elevation view of a test apparatus constructed in accordance with aspects of the invention and which is illustrative of an optical fiber shape sensing system used in a kinematic chain. A first bracket 100a is fixed to a test bench (not shown), and a second bracket 100b is coupled to bracket 100a at a single-DOF revolute joint 102. Bracket 100b is coupled to servomotor 104, which moves bracket 100b with reference to bracket 100a in a conventional manner.

A fiber Bragg grating-configured, three-core optical glass fiber 106 is used in a shape sensing system for the test apparatus. At the proximal end of fiber 106, each core is coupled to a strain interrogation unit 108, which is used in the process of determining the fiber's shape, and consequently the shape of an associated kinematic chain in accordance with known methods. Such methods include optical time domain reflectometry and optical frequency domain reflectometry as described in U.S. Pat. No. 5,798,521 (filed 27 Feb. 1997) and U.S. Pat. Application Publ. No. US 2007/0065077 (filed 26 Sep. 2006), both of which are incorporated by reference. In one implementation the interrogation unit used was an "Optical Backscatter Reflectometer" and associated software supplied by Luna Innovations Incorporated, Roanoke, Va.

The fiber 106 passes through an optical stage 108, which is supported by bracket 100a and which allows adjustments in fiber position (x, y, z) and roll orientation. Optical stage 108 supports a collet (not visible), which in turn holds a fixture 110 as described above. In one test implementation, the fixture portion 110 was as described above with reference to FIG. 4.

The fiber 106 continues through the joint and is held in another fixture 112. The fiber may terminate at fixture 112, in which case it may be held in a manner similar to that shown and described with reference to FIG. 2B. Alternately, the fiber may continue through bracket 100b (the second link), in which case fixture 112 may be configured in accordance with aspects of the invention to avoid the localized saturation problem where the fiber enters the link.

For the shape memory alloy aspect as describe above with reference to FIG. 6, the test apparatus may be modified so that the shape memory alloy tube extends between brackets 100a and 100b, and there is no curved lip to the channel defined in the fixture portion 110.

Figure 9:
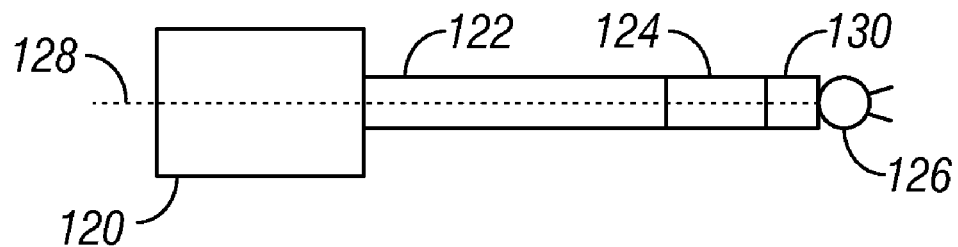
FIG. 9 is a diagrammatic view of a minimally invasive surgical instrument.

FIG. 9 is a diagrammatic view of a minimally invasive surgical instrument, such as various grasping, cutting, scissors, retraction, and the like instruments available for use with the da Vinci® Surgical System. The surgical instrument functions as a kinematic chain in the surgical system. Details of such instruments are available in various United States Patents. Briefly, a transmission mechanism 120 receives mechanical forces for telerobotically controlled servomotor actuators. The transmission mechanism 120 transmits the mechanical forces through a hollow instrument shaft 122 via cables and/or cable/hypotube assemblies to actuate both a wrist mechanism 124 and an end effector 126 at the distal end of the instrument. The wrist mechanism may be a clevis-type mechanism, or it may be a snake-like mechanism. Examples of such wrist mechanisms may be found in U.S. Pat. No. 6,394,998 (filed 17 Sep. 1999) and U.S. Pat. No. 6,817,974 (filed 28 Jun. 2002), both of which are incorporated herein by reference. In accordance with aspects of the invention, a shape sensing optical fiber 128 (shown in dashed line) is routed through or along instrument shaft 122 and wrist mechanism 124 (which may be modeled as one or more joints) to terminate at distal link 130 or end effector 126. As described above, the shape of optical fiber 128 may be determined from sensed strain information and instrument's kinematic pose may be then determined using inverse kinematic calculations. FIG. 9 is further illustrative of other instruments and devices that may be used during surgery, such as the various rigid-link and flexible devices illustrated in U.S. Pat. Application Publ. No. 2008/0065105 (filed 13 Jun. 2007), which is incorporated herein by reference.

We claim:

1. An apparatus comprising:
 a first link, a second link, and a joint coupled between the first and second links configured to permit relative articulation of the first link and the second link;
 a shape memory alloy tube extending between the first link and the second link, the tube passing through an opening surrounded by a lip and extending from the first link into the joint; and
 a shape-sensing optical fiber extending through the shape memory alloy tube, wherein the optical fiber comprises a length of fiber containing fiber Bragg gratings positioned adjacent the lip.

2. The apparatus of claim 1:
 wherein the shape memory alloy comprises a Nickel/Titanium alloy.

3. A method comprising:
 assembling a first link, a second link, and a joint coupled between the first and second links configured to permit relative articulation of the first link and the second link;
 extending a shape memory alloy tube between the first link and the second link, wherein the tube passes through an opening surrounded by a lip and extending from the first link into the joint; and
 positioning a shape-sensing optical fiber through the shape memory alloy tube, wherein the optical fiber comprises a length of fiber Bragg gratings positioned adjacent the lip.

4. The method of claim 3:
 wherein the shape memory alloy comprises a Nickel/Titanium alloy.

5. The method of claim 3 further comprising:
 constraining the optical fiber to slide longitudinally with reference to the first link.

6. The method of claim 3 further comprising:
 constraining the optical fiber to be fixed with reference to the first link.

7. The apparatus of claim 1:
 wherein the shape memory alloy tube provides an effective minimum bend radius for the shape-sensing optical fiber of less than about 10 mm.

8. The method of claim 3:
 wherein positioning the shape-sensing optical fiber through the shape memory alloy tube provides an effective minimum bend radius for the shape-sensing optical fiber of less than about 10 mm.

9. An apparatus comprising:
 a first link, a second link, and a joint coupled between the first and second links and configured to permit relative articulation of the first link and the second link;
 a tube extending between the first link and the second link, and passing through an opening surrounded by a lip and extending from the first link into the joint; and
 a shape-sensing optical fiber extending through the tube, wherein as the optical fiber bends, the tube distributes a force exerted by the lip along the optical fiber sufficient to avoid producing a region of local strain along a portion of the optical fiber that is adjacent the lip.

10. The apparatus of claim 9:
 wherein the tube comprises a shape memory alloy.

11. The apparatus of claim 10:
 wherein the shape memory alloy comprises a Nickel/Titanium alloy.

12. The apparatus of claim 9:
 wherein the tube provides an effective minimum bend radius for the shape-sensing optical fiber of less than about 10 mm.

13. A method comprising:
 articulating a first link and a second link relative to each other via a joint coupled between the first and second links;
 sensing a position of the first link and the second link relative to each other via a shape-sensing optical fiber that extends between the first link and the second link, and passes through an opening defining a lip and extending from the first link into the joint; and
 during bending of the optical fiber, distributing a force exerted by the lip along the optical fiber via a tube surrounding the optical fiber;
 wherein the optical fiber comprises a length of fiber containing fiber Bragg gratings positioned adjacent the lip; and
 wherein distributing the force exerted by the lip comprises distributing the force along the optical fiber to avoid producing a region of local strain in the length of fiber containing the fiber Bragg gratings.

14. The method of claim 13:
 wherein the tube comprises a shape memory alloy.

15. The method of claim 13:
 wherein the shape memory alloy comprises a Nickel/Titanium alloy.

16. The method of claim 13 further comprising:
 constraining the optical fiber to slide longitudinally relative to the first link.

17. The method of claim 13 further comprising:
 constraining the optical fiber to be fixed relative to the first link.

18. The apparatus of claim 1:
 wherein a limit range of motion of the joint defines a minimum bend radius of the shape-sensing optical fiber, and wherein the shape memory alloy tube provides an effective minimum bend radius for the shape-sensing optical fiber that is larger than the defined minimum bend radius of the shape-sensing optical fiber.

19. The apparatus of claim 9:
 wherein a limit range of motion of the joint defines a minimum bend radius of the shape-sensing optical fiber, and wherein the tube provides an effective minimum bend radius for the shape-sensing optical fiber that is larger than the defined minimum bend radius of the shape-sensing optical fiber.

* * * * *